(12) United States Patent
Keenan (10) Patent No.: US 8,865,957 B2
(45) Date of Patent: Oct. 21, 2014

(54) METHOD FOR PRODUCING ALPHA-METHYL STYRENE FROM CUMENE

(71) Applicant: Honeywell International Inc., Morristown, NJ (US)

(72) Inventor: Scott R. Keenan, Marlton, NJ (US)

(73) Assignee: Honeywell Intenational Inc., Morristown, NJ (US)

( * ) Notice: Subject to any disclaimer, the term of this patent is extended or adjusted under 35 U.S.C. 154(b) by 43 days.

(21) Appl. No.: 13/761,642

(22) Filed: Feb. 7, 2013

(65) Prior Publication Data

US 2013/0237736 A1 Sep. 12, 2013

Related U.S. Application Data

(60) Provisional application No. 61/608,811, filed on Mar. 9, 2012.

(51) Int. Cl.
*C07C 1/20* (2006.01)
*C07C 1/24* (2006.01)
*C07C 7/20* (2006.01)
*C07C 7/04* (2006.01)

(52) U.S. Cl.
CPC ... *C07C 1/20* (2013.01); *C07C 7/20* (2013.01); *C07C 7/04* (2013.01)
USPC .......................... 585/435; 585/436; 585/437

(58) Field of Classification Search
CPC ............. C07C 7/20; C07C 1/20; C07C 7/04; C07C 15/44
USPC .......................................... 585/435, 436, 437
See application file for complete search history.

(56) References Cited

U.S. PATENT DOCUMENTS

| | | | |
|---|---|---|---|
| 3,646,235 A | 2/1972 | Little et al. |
| 3,965,187 A | 6/1976 | Little et al. |
| 4,088,703 A | 5/1978 | Yeh et al. |
| 4,634,796 A | 1/1987 | Suciu et al. |
| 4,851,086 A | 7/1989 | Khonsari et al. |
| 5,064,507 A | 11/1991 | O'Donnell et al. |
| 5,254,751 A | 10/1993 | Zakoshansky |
| 5,371,305 A | 12/1994 | Hood |

(Continued)

FOREIGN PATENT DOCUMENTS

| | | |
|---|---|---|
| EP | 1411040 B1 | 7/2010 |
| WO | WO 2012/036819 | 3/2012 |

OTHER PUBLICATIONS

Goh et al., Miscible Blends of Poly(styrene-co-Acrylonitrile) and Poly(a-Methyl Styrene-co-Acrylonitrile) with Poly(methyl Methacrylate) Containing Sterically Hindered Amine Group, Journal of Applied Polymer Science, vol. 31, (1986), pp. 2055-2060.

(Continued)

*Primary Examiner* — Thuan D Dang
(74) *Attorney, Agent, or Firm* — Faegre Baker Daniels LLP (57) ABSTRACT

A method for controlling the production of heavy compounds in the production of alpha-methyl styrene is provided. In one embodiment, the method includes providing a first composition to a distillation column, said first composition comprising acetone, phenol, cumene and alpha-methyl styrene; refining the first composition in the distillation column to produce a second composition comprising at least 1 wt. % alpha-methyl styrene and at least one organic acid, wherein the second composition includes a higher weight percentage of alpha-methyl styrene than the first composition; and adding an amine to the second composition.

20 Claims, 6 Drawing Sheets

(56) References Cited

U.S. PATENT DOCUMENTS

| | | |
|---|---|---|
| 5,430,200 A | 7/1995 | Hood |
| 5,463,136 A | 10/1995 | Blackbourn et al. |
| 5,998,677 A | 12/1999 | Yasaka et al. |
| 6,057,483 A | 5/2000 | Zakoshansky |
| 6,201,157 B1 | 3/2001 | Keenan |
| 6,225,513 B1 | 5/2001 | Zakoshansky |
| 6,252,124 B1 | 6/2001 | Zakoshanski et al. |
| 6,307,112 B1 | 10/2001 | Weber et al. |
| 7,109,385 B2 | 9/2006 | Tatake et al. |
| 7,482,493 B2 | 1/2009 | Nelson et al. |
| RE40,668 E | 3/2009 | Zakoshansky |
| 7,902,408 B2 | 3/2011 | Palmer |
| 2011/0301387 A1 | 12/2011 | Wang et al. |
| 2011/0306800 A1 | 12/2011 | Keenan et al. |

OTHER PUBLICATIONS

PCT ISR & Written Opinion issued in PCT/US2013/028498 dated Jun. 28, 2013.

METHOD FOR PRODUCING ALPHA-METHYL STYRENE FROM CUMENE

CROSS-REFERENCE TO RELATED APPLICATIONS

This application claims the benefit under 35 U.S.C. §119 (e) of U.S. Provisional Patent Application Ser. No. 61/608,811 filed Mar. 9, 2012, the disclosure of which is hereby incorporated by reference in its entirety.

TECHNICAL FIELD

The present technology relates to methods of producing alpha-methyl styrene and other products from cumene.

BACKGROUND

The dominant commercial method for producing phenol and acetone is by air oxidation of cumene to cumene hydroperoxide (CHP), followed by acid catalyzed decomposition of the CHP very selectively to phenol and acetone. Dimethylbenzyl alcohol (DMBA) is formed as the principle side product in the oxidation step and is subsequently dehydrated to alpha-methyl styrene (AMS) in the same acid catalyzed decomposition step. AMS is used commercially in the manufacture of plasticizers, resins and other polymers.

A variety of ways to purify the components of the crude product formed from acid catalyzed decomposition of cumene hydroperoxide mixtures are known. Most commercial processes utilize a two step, continuous flow approach to optimize overall yield in this step, especially of DMBA to AMS. Detailed descriptions of this process are disclosed in, e.g., U.S. Pat. Nos. 7,482,493; 7,109,385; 6,307,112; 6,225,513; 6,201,157; 6,057,483; 5,998,677; 5,463,136; 5,430,200; 5,371,305; 5,254,751; 5,064,507; 4,851,086; 4,634,796; and 4,358,618, each of which are incorporated herein by reference in their entirety. In another method, phenol and heavy components are separated from the rest of the mixture, which contains AMS, in a single distillation step.

In both approaches there is a stream, or location in a column, where AMS and phenol concentrate in the presence of organic acids resulting in the formation of undesirable heavy compounds which are lower value by-products that generally require further processing. In addition, these organic acids, such as formic acid and acetic acid, can generate a corrosive environment. Examples of heavy compounds include but are not limited to ortho- and para-cumyl phenol and dimers of AMS.

SUMMARY

The disclosure pertains to methods for controlling the production of heavy compounds in the production of alpha-methyl styrene from cumene.

Accordingly, some embodiments pertain to a method for producing alpha-methyl styrene from cumene in which a first composition is provided to a distillation column, said first composition comprising acetone, phenol, cumene and alpha-methyl styrene. The first composition is refined in the distillation column to produce a second composition comprising at least 1 wt. % alpha-methyl styrene and at least one organic acid, wherein the second composition includes a higher weight percentage of alpha-methyl styrene than the first composition. An amine is added to the second composition.

The method may include refining the second composition in a second distillation column to produce an overheads stream enriched in alpha-methyl styrene and a bottoms stream depleted in alpha-methyl styrene, wherein the bottoms stream further includes at least one heavy compound. The at least one heavy compound may be selected from the group consisting of ortho-cumyl phenol, para-cumyl phenol, alpha-methyl styrene dimers, cumylphenyl ether, acetol derived oxygenates, and combinations thereof. The at least one heavy compound may have a molecular weight of 150 or greater.

The adding step may include adding the amine to a feed stream of the second distillation column, to an overheads stream of the distillation column including the second composition, or to a zone of the distillation column including the second composition. The amine may be added to the second composition as part of a third composition comprising the amine and at least one heavy compound.

The adding step may include adding between about 0.05 wt. % and 1.0 wt. % or 0.05 wt. % and 0.1 wt. % amine to the second composition based on the total weight of the second composition. The amine may have at least one primary nitrogen group. The amine may be a diamine including two primary nitrogen groups. The amine may be selected from the group consisting of 2-methylpentamethylenediamine, hexamethylenediamine, or combinations thereof. The amine may include an amine compound that is capable of reacting with a carbonyl compound.

The second composition may further comprise at least one compound selected from the group consisting of acetol, cumene, and phenol.

The method may further comprise performing an acid catalyzed decomposition of cumene hydroperoxide and di-methyl benzyl alcohol to produce the first composition. The method may further comprise performing an air-oxidation of cumene to produce the said cumene hydroperoxide and di-methyl benzyl alcohol.

The organic acid may be selected from the group consisting of formic acid and acetic acid. The organic acid may further be selected from oxalic, lactic, maleic, benzoic, succinic, butryic, and other similar mono- or di-acidic organic acids.

In some embodiments, methods for controlling the production of heavy compounds in the production of alpha-methyl styrene from cumene are provided. The method includes performing an air-oxidation reaction of cumene to produce cumene hydroperoxide and di-methyl benzyl alcohol; performing an acid catalyzed decomposition of cumene hydroperoxide to produce a first product stream; refining the first product stream in a first distillation column to produce an overheads stream and a bottoms stream, wherein the overheads stream comprises at least 1 wt. % alpha-methyl styrene and an organic acid and the weight percentage of alpha-methyl styrene for the overheads stream is greater than the weight percentage of alpha-methyl styrene for the bottoms stream; adding a first quantity of amine to overheads stream, wherein the first quantity of amine is between 0.05 wt. % and 1.0 wt. % of the total weight of the overheads stream; and refining the overheads stream in a second distillation column to produce a second overheads stream and a second bottoms stream.

In some embodiments, a method for controlling the production of heavy compounds in the production of alpha-methyl styrene from cumene is provided. The method includes performing an air-oxidation reaction of cumene to produce cumene hydroperoxide and di-methyl benzyl alcohol; performing an acid catalyzed decomposition of cumene hydroperoxide to produce a first product stream; refining the first product stream in a first distillation column to produce a first distillation zone, wherein the distillation zone comprises alpha-methyl styrene and an organic acid; adding a first quantity of amine to the distillation zone, removing a second product stream from the first distillation zone; and refining the first recovery stream in a second distillation column to produce a first refined stream and a bottoms stream. The first quantity of amine is between 0.05 wt. % and 1.0 wt. % of the total weight of the second product stream.

While multiple embodiments are disclosed, still other embodiments of the present invention will become apparent to those skilled in the art from the following detailed description, which shows and describes illustrative embodiments of the invention. Accordingly, the description is to be regarded as illustrative in nature and not restrictive.

DETAILED DESCRIPTION

Figure 1:
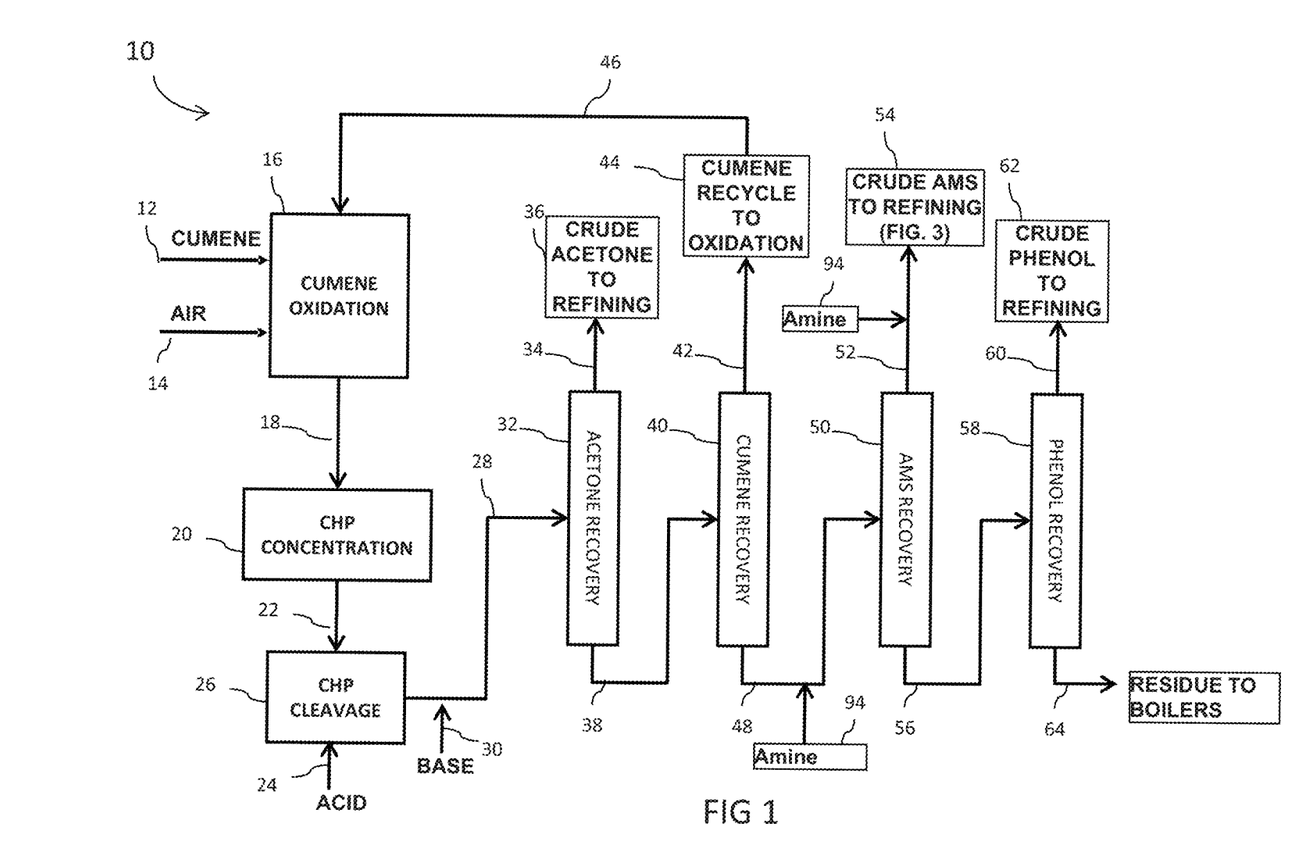
FIG. 1 is a schematic illustration of a system and process for production of phenol, acetone and alpha-methyl styrene from cumene via air oxidation of cumene, decomposition of the resulting cumene hydroperoxide with a mineral acid, and recovery of the products generated according an embodiment of the invention.

FIG. 1 illustrates part of an exemplary system 10 for producing phenol and acetone via air oxidation of cumene to form cumene hydroperoxide (CHP), followed by acid catalyzed decomposition of the CHP to form phenol and acetone. In some embodiments, dimethylbenzyl alcohol (DMBA) is formed as a principle side product during oxidation but may be dehydrated during the acid catalyzed decomposition step to form alpha-methyl styrene (AMS). In some embodiments, a second composition formed during the decomposition step includes AMS in an amount as little as 1 wt. %, 2.5 wt. %, 5 wt. %, or as high as 10 wt. %, 20 wt. %, 50 wt. %, or within any range defined between any pair of the foregoing values.

In the exemplary embodiment of FIG. 1, cumene 12 and air 14 are provided to a cumene oxidation step or unit 16 where the cumene is oxidized to form cumene hydroperoxide (CHP). A principle side product of this reaction is dimethylbenzyl alcohol (DMBA). Both CHP and DMBA are present in the stream 18 leaving the cumene oxidation step or unit 16. Following oxidation, the CHP is concentrated in CHP concentration step or unit 20. An acid 24 is added to the stream 22 exiting CHP concentration step or unit 20. Exemplary acids include mineral acids such as sulfuric, nitric, phosphoric, and hydrochloric acids and solid acid catalysts, such as sulfonated styrene/divinylbenzene polymer beads and zeolites. The addition of an acid 24 causes the acid catalyzed decomposition of CHP to form phenol and acetone in CHP cleavage step or unit 26. The DMBA may be dehydrated during the acid catalyzed decomposition step to form alpha-methyl styrene (AMS). A base 30 is added to the stream 28 exiting CHP cleavage step or unit 26. Exemplary bases include amine compounds such as ammonia, hexamethylenediamine, 2-methyl-1,5-diaminopentane, 2-methylpentamethylenediamine, and ethylene amines, and solid basic ion exchange resins.

In the exemplary embodiment shown in FIG. 1, a plurality of distillation columns separate each component by boiling point. The inlet stream 28 to acetone recovery column 32 separates crude acetone through the overheads stream 34 to be sent for further refining 36. The bottoms stream 38 from acetone recovery column 32 is fed to cumene recovery column 40, which separates cumene through the overheads stream 42 and recycles the cumene through recycle stream 46 to cumene oxidation step or unit 16. Although not shown, recycle stream 46 may include additional refining steps or units prior to being reintroduced to cumene oxidation step or unit 16. The bottom stream 48 is fed to AMS recovery column 50, which separates crude AMS through the overheads stream 52 to be sent for further refining 54 (see FIG. 3). The bottoms stream 56 of AMS recovery column 50 is fed to phenol recovery column 58, which separates crude phenol through the overheads stream 60 to be sent for further refining 62. The bottoms stream 64 of phenol recovery column 58 is illustratively sent to boilers.

The overheads stream 52 exiting AMS recovery column 50, for example, may include from about 15 to 75 wt. % AMS and about 25 to 85 wt. % phenol, in addition to from about 0.5 wt. % to about 5 wt. % of cumene, 1000 or more parts per million (ppm) hydroxyacetone (acetol), and about 100 or more ppm organic acids such as formic acid and acetic acid. The overheads stream 52 exiting AMS recovery column 50 is delivered to an AMS refining process 54 (see FIG. 3) for further processing. It will be appreciated that additional processing steps may occur prior to the overheads stream 52 entering the AMS refining process 54.

Figure 2:
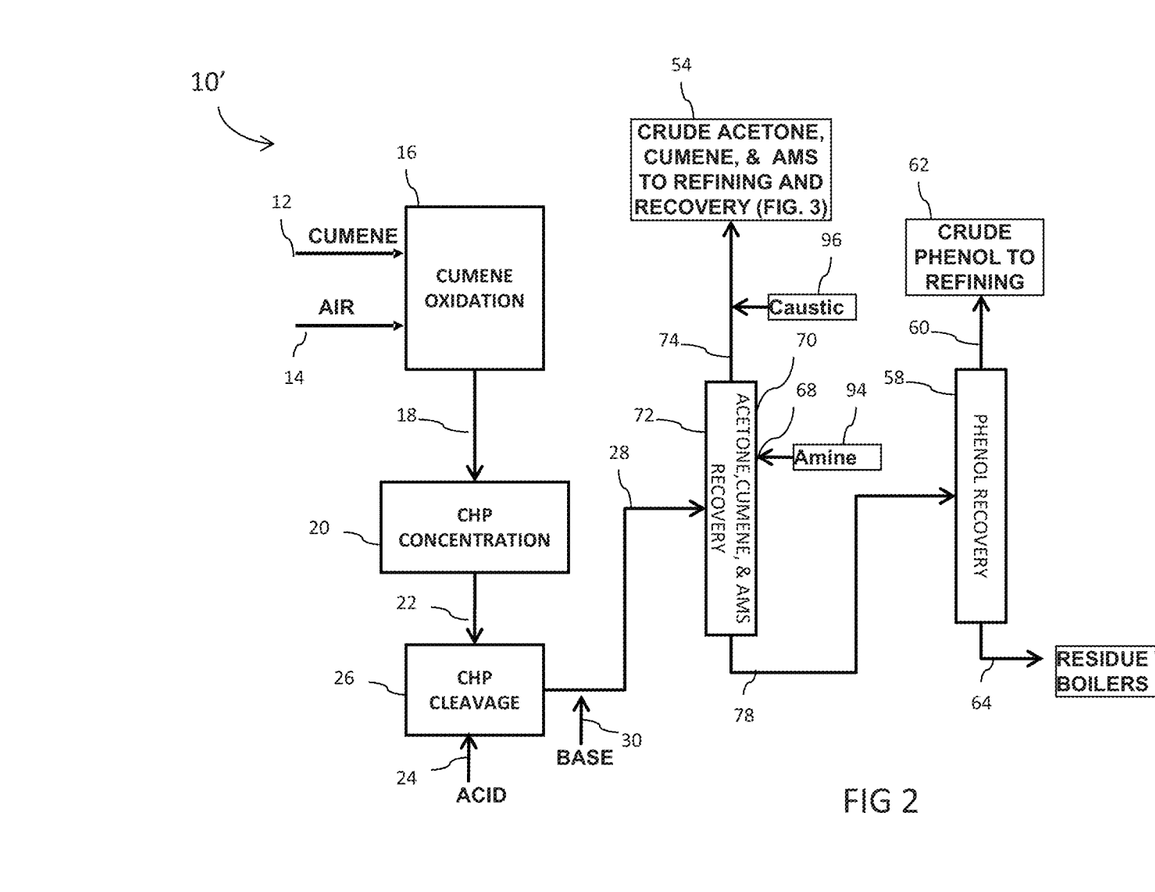
FIG. 2 is a schematic illustration of a system and process for production of phenol, acetone and alpha-methyl styrene from cumene via air oxidation of cumene, decomposition of the resulting cumene hydroperoxide with a mineral acid, and recovery of the products generated according to another embodiment of the invention.

FIG. 2 illustrates a portion of an exemplary alternative system 10' for the production of AMS, phenol and acetone from cumene hydroperoxide (CHP). Alternate system 10' is similar to exemplary system 10 illustrated in FIG. 1, but acetone recovery column 32, cumene recovery column 40, and AMS recovery column 50 are replaced with a single recovery column 72. In the alternative system 10' shown in FIG. 2, the inlet stream 28 to recovery column 72 separates crude acetone, cumene, and AMS through the overheads stream 74 to be sent to AMS refining process 54 (see FIG. 3) for further processing. The overheads stream 74 exiting recovery column 72 may include AMS, acetone, cumene, acetol, and organic acids. In an embodiment, acetone, AMS, cumene, and acetol are removed from recovery column 72 through overheads stream 74 and treated with caustic 96 to remove aldehydes from the acetone. It will be appreciated that additional processing steps may occur prior to the overheads stream 74 entering the AMS refining process 54. The bottom stream 78 from recovery column 72 is fed to phenol recovery column 58, which separates crude phenol through the overheads stream 60 to be sent for further refining 62. The bottoms stream 64 is illustratively sent to boilers.

Figure 3:
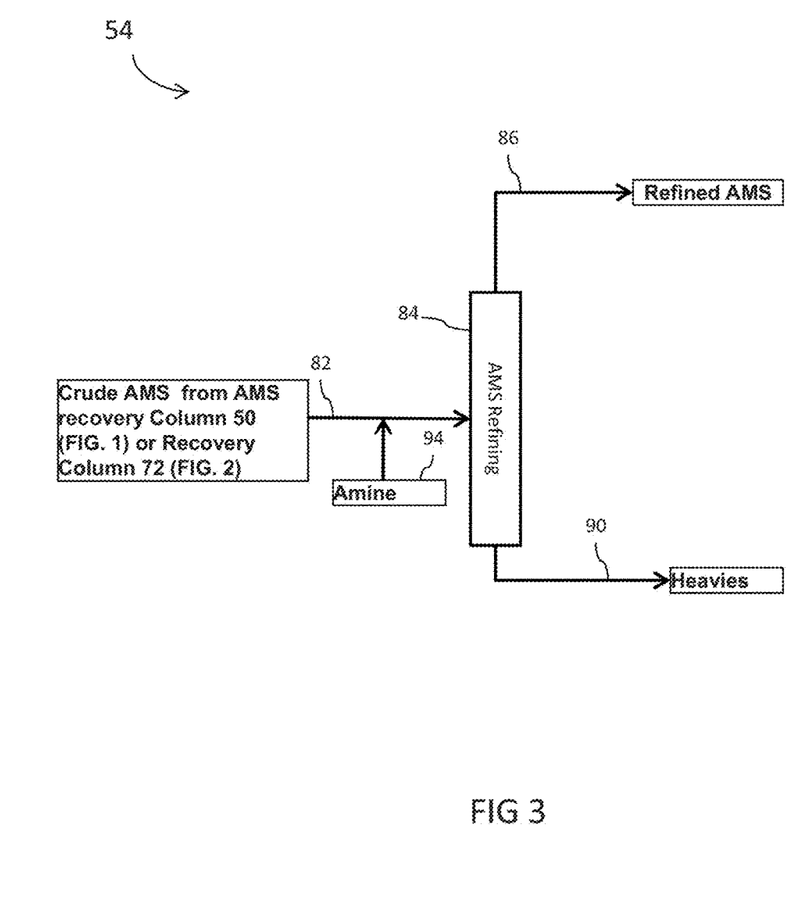
FIG. 3 is a schematic illustration of a system and process for further refining alpha-methyl styrene according to another embodiment of the invention.

FIG. 3 illustrates a portion of a system 80 for refining crude AMS produced according to system 10 or alternative system 10' discussed herein. The AMS composition 80 is provided to a AMS refining column 84 through a feed stream 82. The feed stream 82 may be an overheads stream 52 from AMS recovery column 50 or an overheads stream 74 from recovery column 72. It will be appreciated that additional processing steps may occur prior to the feed stream 82 entering the AMS refining column 84. The AMS refining column 84 separates the AMS, which exits the AMS refining column through overheads stream 86, from additional by-products including heavy compounds, such as cumyl phenols and AMS dimers, which exit the refining column 84 through the bottoms stream 90.

In one embodiment, an amine is added to a stream containing AMS in an amount as little as 0.1 wt. %, 0.5 wt. %, 1 wt. %, 2.5%, 5 wt. %, or as high as 10 wt. %, 20%, 50 wt. %, or within any range defined between any pair of the foregoing values. Exemplary amines are of the formula:

(I)

where $R_1$, $R_2$, and $R_3$ are independently selected from H and organic groups. Where exactly two of $R_1$, $R_2$, and $R_3$ are hydrogen, the amine contains a primary nitrogen group. Where exactly one of $R_1$, $R_2$, and $R_3$ is hydrogen, the amine contains a secondary nitrogen group. Where none of $R_1$, $R_2$, and $R_3$ are hydrogen, the amine contains a tertiary nitrogen group. Where one of $R_1$, $R_2$, and $R_3$ includes an amine, the amine is a diamine.

A wide range of amines may be used according to embodiments of the present invention. In one embodiment, the amine is a primary amine having at least one primary nitrogen group, capable of reacting with the acetol present in the reflux or overheads stream. In another embodiment, the amine is a diamine having two primary nitrogen groups. In a further embodiment, the amine is a methyl-branched diamine, such as 2-methylpentamethylenediamine, commercially available under the trade name Dytek A, or hexamethylene diamine, available under the trade name Dytek E. However, one of skill in the art will realize that any amine capable of neutralizing organic acids, such as formic acid and acetic acid, and/or reacting with carbonyl compounds such as acetol may be used.

In an embodiment, an amine is added directly to the reflux of a column containing AMS. In another embodiment, an amine is added directly to the overheads stream including AMS prior to refining. The reflux and overheads streams containing AMS may each be referred to as an AMS composition.

The amine may be added in a sufficient amount to neutralize at least a portion of the organic acids present in the AMS composition. In addition, a primary amine may react with acetol present in AMS composition, decreasing the concentration of acetol in the AMS composition.

In some embodiments, the heavy compound is ortho-cumyl phenol, para-cumyl phenol, alpha-methyl styrene dimers, cumylphenyl ether, acetol derived oxygenates, or combinations thereof. In some embodiments, the heavy compounds have a molecular weight greater than 150, 180, 200, 210, 250, 320 or within a range defined between any pair of the foregoing values.

The amount of amine added to the reflux or overheads stream may vary depending on the component concentration of the AMS composition to which the amine is being added. In some embodiments, the amine may be added in an amount that results in the AMS composition including between about 0.05 wt. % to 1.0 wt. % amine. In some embodiments, the amine may be added in an amount as little as 0.01 wt. %, 0.05 wt. %, 0.1 wt. %, 0.2 wt. %, 0.5 wt. %, 1 wt. %, or within any range defined between any pair of the foregoing values.

In a conventional processes, acetol, which follows the overheads stream 74 of recovery column 72 and may be present in the overhead stream 52 of AMS recovery column 50, may react with the AMS composition to form oxygenates, such as 3-methyl-cyclopent-2-eneone, when exposed to caustic catalyst. These impurities may end up in the AMS product and impact downstream end uses. However, the addition of the amine neutralizes at least a portion of the organic acids, and reacts with the acetol, reducing or preventing the formation of acetol derived oxygenates via caustic catalysis.

In one embodiment, adding an amine 94 prior to refining provides for higher AMS recovery and lower heavies production. In some embodiments, the amine may be added in an amount that results in the AMS composition including between about 0.05 wt. % to 1.0 wt. % amine. In some embodiments, the amine may be added in an amount as little as 0.01 wt. %, 0.05 wt. %, or as high as 0.1 wt. %, 0.5 wt. %, 1 wt. %, or within any range defined between any pair of the foregoing values.

Referring to FIG. 1, in one embodiment, the amine 94 may be added to the overheads stream 52 exiting AMS recovery column 50. In one embodiment, amine 94 may be added to bottoms stream 48 fed to AMS recovery column 50. Referring to FIG. 2, in one embodiment, the amine may be added to the reflux of column 72 at a zone 68 in the recovery column 72 containing as little as 1 wt. %, 2.5%, 5 wt. %, or as high as 10 wt. %, 20%, 50 wt. % AMS, and in a more particular embodiment between about 1 to 10 wt. % AMS, in which varying levels of acetone, phenol, cumene, acetol and organic acids are present. In one embodiment, the amine is added in a cumene zone 70 of the recovery column 72, located above zone 68, which may result in the amine moving down the recovery column 72 into the AMS zone. Referring to FIG. 3, in one embodiment, the amine may be added to the feed stream 82 to AMS refining column 84.

Example 1

The experiment was performed on a multi-step refining facility similar in operation to the process shown in FIG. 1. The facility included two parallel distillation columns (Column A and Column B, represented by column 50 in FIG. 1) in which the overheads streams were sent for AMS refining to column 84 in FIG. 3. Column A had a flow rate of about 1400 gallons per hour and column B had a flow rate of about 2000 gallons per hour. Dytek A amine was added to both columns by attaching positive displacement pumps to the overhead control valves of each column. In the first trial, illustrated as days 4 and 5 in FIG. 4, the injection rate was 2.4 gallons per hour (about 9.1 liters per hour) for column A and 3.6 gallons per hour (about 13.6 liters per hour) for column B, resulting in a concentration of about 0.2 wt. % amine in the overheads stream. In the second trial, illustrated as days 8 and 9 in FIG. 4, the total injection rate was about 3 gallons per hour, resulting in a concentration of about 0.1 wt. % amine in the overheads stream. Samples were collected from the feed, overheads and bottoms stream of the AMS refining column every 12 hours prior to, during and after injection of the amine. The bottom samples were tested for heavies content via gas chromatography. The feed and overheads samples were pH tested using direct immersion of a combination electrode.

Figure 4:
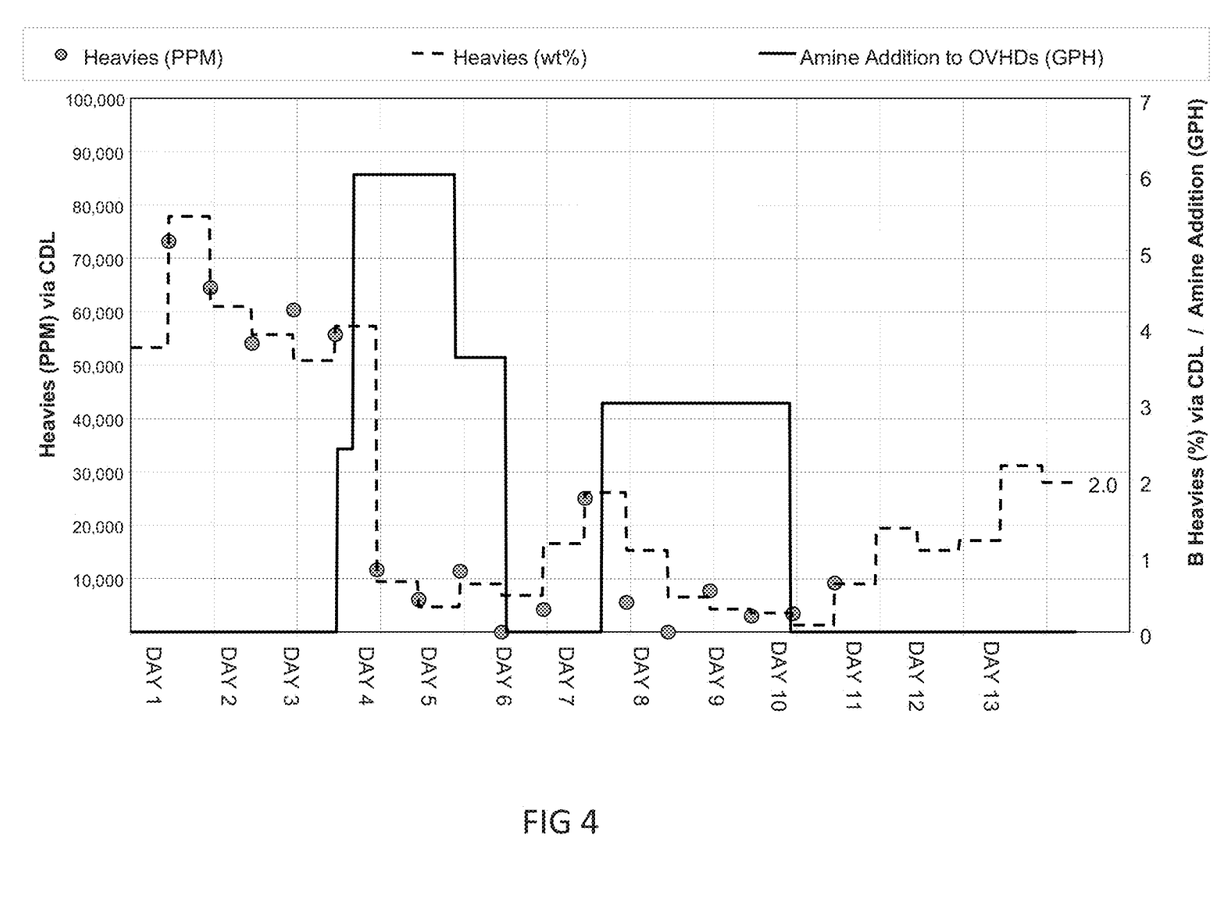
FIG. 4 is a graph illustrating experimental results associated with Example 1 according to embodiments of the present invention.

FIG. 4 illustrates the results of the experiment with respect to heavies formation. Prior to adding amine to the overheads streams of columns A & B, the AMS refining column 84 averaged 4.0 wt. % heavies. During the periods when amines were added, the heavies content averaged only 0.5 wt. %. Prior to adding amines to the overheads stream of columns A and B, the average pH of the feed stream 82 to AMS refining column 84 was 4.4 and the average pH of the overheads stream 86 was 5.5. When amines were added, the average pH of the feed stream 82 was 6.0 and the average pH of the overheads stream 86 was 7.1.

The reduction in heavies content indicates that a smaller amount of AMS reacted with itself or phenol to form heavy compounds due to reduction of the amount of acids present during AMS distillation, resulting in improved AMS yield. The shift in the pH of the feed and overhead streams shown in FIG. 4 also clearly indicates that significant amounts of the organic acids were neutralized.

Example 2

Organic acids present in the overheads obtained from columns 50, 72, and 84 promote the reaction of AMS and phenol to heavies. The high acidity in these overheads is also responsible for the corrosion in columns 50, 72, and 84. It was desired to determine if the acidity from the organic acids present in the overheads could be neutralized by feeding an amine-containing stream to the overheads of column 50 or 72 feeding AMS refining column 84.

A laboratory study was carried out, in which a first amine-containing stream comprised of was blended with a second AMS-containing stream comprised of 40 wt % AMS and 50 wt % phenol, such as obtained from two parallel distillation columns (represented by column 54 in FIG. 1). Changes in the impurity profile were monitored over time. The study involved blends of 0, 5, 10, and 20 wt % of the first amine-containing stream, with the remainder being the second AMS-containing stream.

For each run, approximately 20 g of the blend was placed in a 50 mL jacketed open glass vessel and allowed to reach the set temperature of 80° C. Each run was sampled at 0, 15, 30, 45 and 60 min, at which time the samples were diluted with approximately 15% n-propyl alcohol and neutralized with soda ash in gas chromatography vials to inhibit further reaction.

The extent of the reactivity of phenol and AMS was determined by the formation of cumylphenyl ether (CPE), AMS dimers, and cumylphenols. Of these, the impurity of most interest was CPE since it is the kinetic product, and hence the product formed first, which would react and rearrange further with time to form other products.

Figure 5:
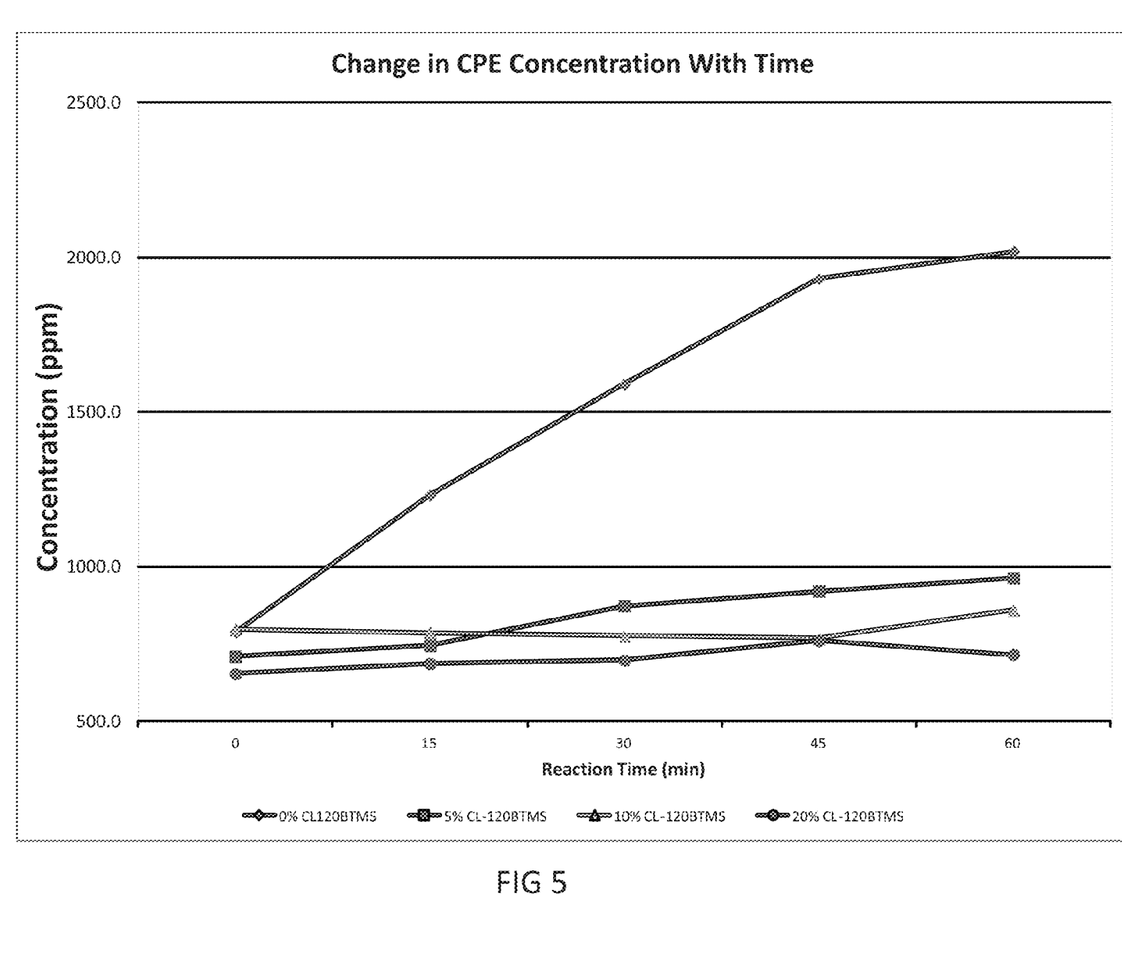
FIG. 5 is a graph showing the formation of CPE as a function of time and is associated with Example 2.
Figure 6:
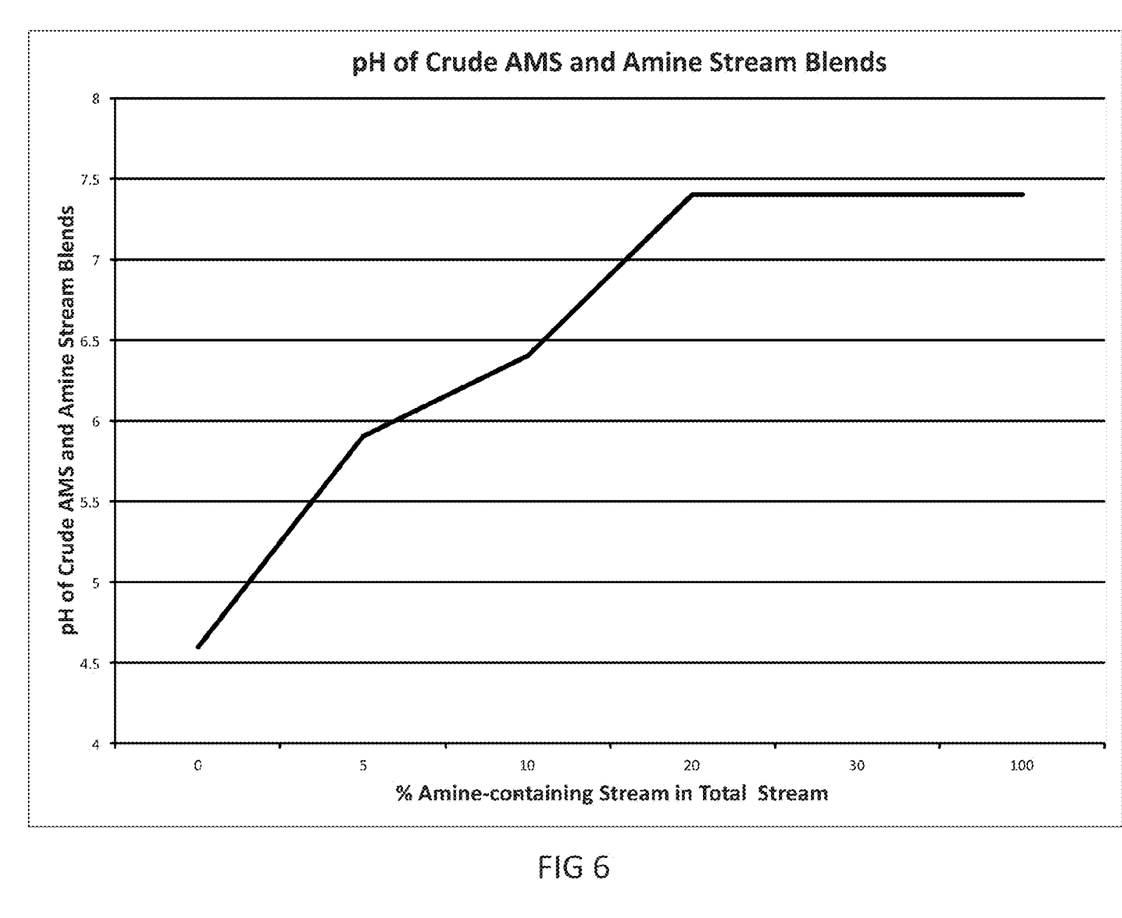
FIG. 6 is a graph showing the increase in pH as a first amine-containing stream is blended into a second AMS-containing stream and is associated with Example 2.

FIG. 5 shows the formation of CPE as a function of time for the blends containing 0, 5, 10, and 20 wt. % of the first amine-containing stream with the second AMS-containing stream. As shown in FIG. 5, for the run containing no amine, CPE concentration rises rapidly from ~800 ppm to over 2000 ppm in 60 min, while at 5% of the first amine-containing stream, CPE increases only from ~750 ppm to ~960 ppm. With 10% and 20% of the first amine-containing stream, the rise in CPE was lower, 800 to 850 ppm and 650 to 710 ppm respectively, confirming the effect of the amine i in controlling the acidity in the second AMS-containing stream. As shown in FIG. 6, this is consistent with the increase in pH as the first amine-containing stream is blended into the second AMS-containing stream, rising from 4.6 in the sample containing 0% of the amine-containing stream to 7.4 at the sample containing 20% of the amine-containing stream.

The following is claimed:

1. A method for controlling the production of heavy compounds in the production of alpha-methyl styrene comprising:
   providing a first composition to a distillation column, said first composition comprising acetone, phenol, cumene and alpha-methyl styrene;
   refining the first composition in the distillation column to produce a second composition comprising at least 1 wt. % alpha-methyl styrene and at least one organic acid, wherein the second composition includes a higher weight percentage of alpha-methyl styrene than the first composition; and
   adding an amine to the second composition.

2. The method of claim 1, further comprising the step of refining the second composition in a second distillation column to produce an overheads stream enriched in alpha-methyl styrene and a bottoms stream depleted in alpha-methyl styrene, wherein the bottoms stream further includes at least one heavy compound.

3. The method of claim 2, wherein the at least one heavy compound is selected from the group consisting of ortho-cumyl phenol, para-cumyl phenol, alpha-methyl styrene dimers, cumylphenyl ether, acetol derived oxygenates, and combinations thereof.

4. The method of claim 2, wherein said at least one heavy compound has a molecular weight of 150 or greater.

5. The method of claim 2, wherein said adding step includes adding the amine to a feed stream of the second distillation column.

6. The method of claim 1, wherein said adding step includes adding the amine to an overheads stream of the distillation column including the second composition.

7. The method of claim 1, wherein said adding step includes adding the amine to a zone of the distillation column including the second composition.

8. The method of claim 1, wherein the adding step comprises adding between about 0.05 wt. % and 1.0 wt. % amine to the second composition based on the total weight of the second composition.

9. The method of claim 1, wherein the adding step comprises adding between about 0.05 wt. % and 0.1 wt. % amine to the second composition based on the total weight of the second composition.

10. The method of claim 1, wherein the amine comprises at least one primary nitrogen group.

11. The method of claim 1, wherein the amine comprises a diamine including two primary nitrogen groups.

12. The method of claim 1, wherein the amine is selected from the group consisting of 2-methylpentamethylenediamine, hexamethylenediamine, or combinations thereof.

13. The method of claim 1, wherein the amine is added to the second composition as part of a third composition comprising the amine and at least one heavy compound.

14. The method of claim 1, wherein the amine comprises an amine compound that is capable of reacting with a carbonyl compound.

15. The method of claim 1, wherein the second composition further comprises at least one compound selected from the group consisting of acetol, cumene, and phenol.

16. The method of claim 1, further comprising the step of performing an acid catalyzed decomposition of cumene hydroperoxide and di-methyl benzyl alcohol to produce the first composition.

17. The method of claim 16, further comprising the step of performing an air-oxidation of cumene to produce the said cumene hydroperoxide and di-methyl benzyl alcohol.

18. The method of claim 1, wherein the organic acid is selected from the group consisting of formic acid, acetic acid, oxalic acid, lactic acid, maleic acid, benzoic acid, succinic acid, and butryic acid.

19. The method of claim 1, further comprising:
performing an air-oxidation reaction of cumene to produce cumene hydroperoxide and di-mehtyl benzyl alcohol; and
performing an acid catalyzed decomposition of cumene hydroperoxide to produce the first composition;
wherein said adding step includes adding the amine to an overheads stream of the distillation column including the second composition.

20. The method of claim 1, further comprising:
performing an air-oxidation reaction of cumene to produce cumene hydroperoxide and di-methyl benzyl alcohol; and
performing an acid catalyzed decomposition of cumene hydroperoxide to produce the first composition;
wherein said adding step includes adding the amine to a zone of the distillation column including the second composition.

\* \* \* \* \*